US012788888B2

(12) United States Patent
Dasbach et al.

(10) Patent No.: US 12,788,888 B2
(45) Date of Patent: Nov. 10, 2026

(54) INJECTOR DEVICE

(71) Applicant: Sanofi, Paris (FR)

(72) Inventors: Uwe Dasbach, Frankfurt am Main (DE); Kai Scheinert, Frankfurt am Main (DE); Daniel Auernhammer, Frankfurt am Main (DE); Florian Schauderna, Frankfurt am Main (DE); Thomas Kemp, Herts (GB); Tim Schuller, Herts (GB); Robbie Wilson, Herts (GB); Michael Noble, Herts (GB); Ryan Anthony McGinley, Herts (GB)

(73) Assignee: Sanofi, Paris (FR)

( * ) Notice: Subject to any disclaimer, the term of this patent is extended or adjusted under 35 U.S.C. 154(b) by 743 days.

(21) Appl. No.: 17/914,897

(22) PCT Filed: Mar. 31, 2021

(86) PCT No.: PCT/EP2021/058507
§ 371 (c)(1),
(2) Date: Sep. 27, 2022

(87) PCT Pub. No.: WO2021/198371
PCT Pub. Date: Oct. 7, 2021

(65) Prior Publication Data

US 2023/0129506 A1 Apr. 27, 2023

(51) Int. Cl.
*A61M 5/20* (2006.01)
*A61M 5/31* (2006.01)

(52) U.S. Cl.
CPC ... *A61M 5/2033* (2013.01); *A61M 2005/3125* (2013.01); *A61M 2205/582* (2013.01); *A61M 2205/583* (2013.01)

(58) Field of Classification Search
CPC .................. A61M 5/24; A61M 5/3157; A61M 2005/3125; A61M 5/2033;
(Continued)

(56) References Cited

U.S. PATENT DOCUMENTS 10,434,262 B2 * 10/2019 Bendek ................ A61M 5/326
2011/0313395 A1 * 12/2011 Krulevitch ........ A61M 5/31525 604/82
(Continued)

FOREIGN PATENT DOCUMENTS

CA 3079357 A1 4/2019
CN 101479001 A 7/2009
(Continued)

OTHER PUBLICATIONS

International Preliminary Report on Patentability in International Appln. No. PCT/EP2021/058507, mailed on Oct. 13, 2022, 11 pages.
(Continued)

*Primary Examiner* — Cris L. Rodriguez
(74) *Attorney, Agent, or Firm* — Fish & Richardson P.C.

(57) ABSTRACT

An injector device comprising an elongate housing having a proximal end and a distal end, and configured to receive a container of medicament, a plunger rod moveable longitudinally within the housing between a primed position and a completed position, the plunger rod being configured to be engageable with a container of medicament. The housing comprises an indicator located in a proximal region of the housing. The indicator comprises a display window located in the proximal region of a side wall of the housing, a projection proximally extending from the plunger rod. The projection is coupled to the plunger rod and is visible through the display window in the primed position. The projection is configured to move between a first indicating
(Continued)

position and a second indicating position to provide a user with information associated with a progress of an injection process dependent upon the longitudinal position of the plunger rod.

13 Claims, 7 Drawing Sheets

(58) Field of Classification Search
CPC ...... A61M 2205/582; A61M 2205/583; A61M 5/2466; A61M 5/31591
See application file for complete search history.

(56) References Cited

U.S. PATENT DOCUMENTS

| | | | | |
|---|---|---|---|---|
| 2012/0283655 | A1* | 11/2012 | Plumptre .......... | A61M 5/31585 604/211 |
| 2013/0211377 | A1* | 8/2013 | Butler ............... | A61M 5/31551 604/207 |
| 2013/0317432 | A1 | 11/2013 | Fabien et al. | |
| 2016/0051765 | A1 | 2/2016 | Morris et al. | |
| 2017/0224926 | A1* | 8/2017 | Dennis, Jr. ........ | A61M 5/31561 |
| 2017/0224934 | A1 | 8/2017 | Shultz et al. | |
| 2017/0361025 | A1* | 12/2017 | Cowe ................ | A61M 5/31595 |
| 2020/0405958 | A1* | 12/2020 | Hacker ............... | A61M 5/2448 |

FOREIGN PATENT DOCUMENTS

| | | | |
|---|---|---|---|
| CN | 102665805 | A | 9/2012 |
| CN | 103764206 | A | 4/2014 |
| CN | 105530970 | A | 4/2016 |
| CN | 106573113 | A | 4/2017 |
| CN | 106999666 | A | 8/2017 |
| CN | 108495668 | A | 9/2018 |
| CN | 108697855 | A | 10/2018 |
| CN | 109843357 | A | 6/2019 |
| JP | 2015-501698 | A | 1/2015 |
| JP | 2017-522976 | A | 8/2017 |
| WO | WO 2007/129106 | A2 | 11/2007 |
| WO | WO 2011/047298 | | 4/2011 |
| WO | WO 2013/034985 | A2 | 3/2013 |
| WO | WO 2013/077800 | A1 | 5/2013 |
| WO | WO2015036346 | A1 | 3/2015 |
| WO | WO 2016/025316 | | 2/2016 |
| WO | WO 2016/083347 | | 6/2016 |
| WO | WO 2016/205403 | A2 | 12/2016 |
| WO | WO2017089257 | A1 | 6/2017 |
| WO | WO 2017/118705 | A1 | 7/2017 |
| WO | WO 2008/005315 | | 1/2018 |
| WO | WO2018077880 | A1 | 5/2018 |
| WO | WO 2021/198371 | A1 | 10/2021 |

OTHER PUBLICATIONS

International Search Report and Written Opinion in International Appln. No. PCT/EP2021/058507, mailed on Jun. 17, 2021, 17 pages.

* cited by examiner

INJECTOR DEVICE

CROSS REFERENCE TO RELATED APPLICATIONS

The present application is the national stage entry of International Patent Application No. PCT/EP2021/058507, filed on Mar. 31, 2021, and claims priority to Application No. EP 20315110.5, filed on Apr. 3, 2020, the disclosures of which are incorporated herein by reference.

TECHNICAL FIELD

The present disclosure relates to an injector device for a medicament.

BACKGROUND

Injection devices, for example auto-injectors, typically have a sealed container of medicament, and a needle for injection of the medicament into a patient. In one type of device, the medicament container may comprise a medicament cartridge and the needle may be initially separated from the cartridge. An initial action moves the cartridge and needle together so that the needle pierces the cartridge. In another type of device, the medicament container may comprise a syringe containing a medicament and the needle may be secured to the syringe. In both cases, a plunger or piston within the cartridge or syringe can then be moved into the cartridge or syringe to dispense medicament through the needle for injection to a patient.

SUMMARY

An object of the present disclosure is to provide an advantageous injector device comprising an elongate housing having a proximal end and a distal end, and configured to receive a container of medicament, a plunger rod moveable longitudinally within the housing between a primed position and a completed position, the plunger rod being configured to be engageable with a container of medicament when received in the housing, wherein the housing comprises an indicator located in the region of the proximal end of the housing, the indicator comprising a display window located in the proximal region of a side wall of the housing, a proximally extending projection extending from the plunger rod, wherein the projection is coupled to the plunger rod, the projection being visible through the display window in at least the primed position, the projection being configured to move between a first indicating position and a second indicating position to provide a user with information associated with the progress of the injection progress dependent upon the longitudinal position of the plunger rod.

In one example, the distal end of the housing is relatively closer to a site of injection and the proximal end is relatively further away from the injection site.

The indicator may further comprise an indication element, the projection being located between the display window and the indication element to obscure a user's view of the indication element in at least the primed position.

The projection may be axially coupled to the plunger rod and configured to move between a first indicating position and a second indicating position when the plunger rod is moved from the primed position to the completed position and wherein movement of the projection towards the second indicating position makes a greater portion of the indication element visible through the display window.

In some examples, when the projection is in the first indication position, a proximal end of the projection is located at a proximal end of the display window.

In one embodiment, when the projection is in the first indicating position, only the projection may be visible through the display window.

In some examples, when the projection is in the second indicating position, a proximal end of the projection is located at a distal end of the display window.

In one embodiment, when the projection is in the second indicating position, only the indication element may be visible in the display window.

In some examples, the projection is rotationally decoupled from the plunger rod such that the projection remains aligned with the display window throughout the injection process.

An inner surface of the housing may comprise a guide mechanism configured to restrict rotational motion of the projection about the longitudinal axis of the plunger rod.

In some embodiments, the housing may further comprise a second indicator comprising a display window in the distal region of the housing, a container of medicament being visible through the second display window when the plunger rod is in its primed position and when the container of medicament is received in the housing, and wherein when the plunger rod is moved longitudinally into the completed position the distal end of the plunger rod is located at the distal end of the second window.

In one embodiment, the plunger rod and the indication element may comprise the same indicia and the projection comprises a different indicia to the plunger rod and indication element.

In other embodiments, the plunger rod and the projection may comprise the same indicia and the indication element may comprise a different indicia to the plunger rod and the projection.

In some embodiments, the injector device may further comprise an external sleeve configured to extend around the housing, the external sleeve being moveable longitudinally from a first position at the proximal end of the housing in which the external sleeve covers the indicator to a second position at the distal end of the housing in which the external sleeve exposes the indicator.

The injector device may further comprise a container of medicament received within the housing between the plunger rod and the distal end of the injector device.

The indicator may comprise a spindle, the spindle comprising a shaft and a dial, wherein the dial is configured to rotate to provide a user with information associated with the progress of the injection process dependent upon the longitudinal position of the plunger rod.

The spindle may be constrained from movement in the longitudinal direction and is rotatable relative to the plunger rod.

The spindle may be prevented from moving in the longitudinal direction by the housing.

The dial may be located at the proximal end of the housing such that the distal surface of the dial contacts the proximal end of the housing and the proximal surface of the dial faces outwardly of the device to provide a user with information associated with the progress of the injection process, in use.

The dial may be located inside the housing at the proximal end of the housing such that a proximal surface of the dial faces out of the housing to provide a user with information associated with the progress of the injection process.

The proximal surface of the dial may comprise a surface formation configured to provide tactile feedback to a user associated with the progress of the injection progress.

The housing may comprise a cover extending from the proximal end of the housing and over the proximal surface of the dial, the cover being configured such that the dial can provide visual feedback to a user associated with the progress of the injection progress.

The dial may be housed inside the proximal end of the housing, and the housing further comprises a display window in its side face through which a side face of the dial can be seen, the side face of the dial comprising indicia configured to provide visual feedback to a user associated with the progress of the injection progress.

The shaft of the spindle may comprise a threaded arrangement configured to engage with a threaded arrangement on the plunger rod such that longitudinal movement of the plunger rod from the primed position towards the completed position is configured to cause the dial of the spindle to rotate.

The threaded arrangement may comprise a continuous thread on at least one of the plunger rod and the shaft of the spindle, the continuous thread being configured to provide constant feedback on the progress of the injection process.

The threaded arrangement may comprise a non-continuous thread on one of the plunger rod and the shaft of the spindle, the non-continuous thread being configured to provide event specific feedback on the progress of the injection process.

The plunger rod may be hollow and comprises an open proximal end configured to receive the shaft of the spindle, the plunger rod comprising a thread on its inner surface and the shaft comprising a thread on its outer surface.

Another object of the present disclosure is to provide a method of using an injector device, the method comprising: actuating the injector device such that a plunger rod is moved longitudinally within the housing from a primed position to a completed position; and providing information associated with the longitudinal position of the plunger rod with an indicator.

These and other aspects of the disclosure will be apparent from and elucidated with reference to the embodiments described hereinafter.

BRIEF DESCRIPTION OF THE FIGURES

Embodiments of the disclosure will now be described, by way of example only, with reference to the accompanying drawings, in which.

DETAILED DESCRIPTION

Figure 1A:
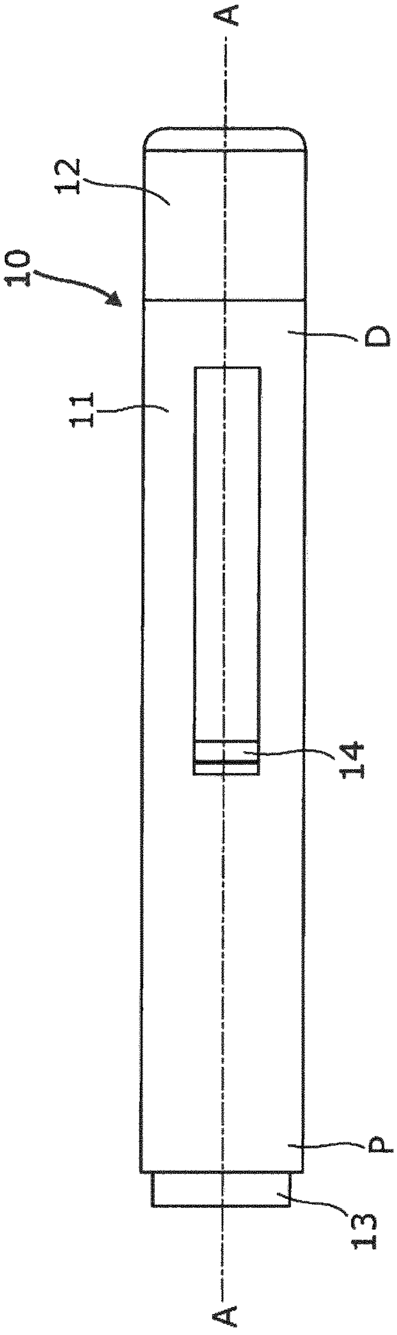
FIG. 1A is a schematic side view of an injector device that embodies the disclosure, and a removable cap.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 3 ml. Another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 50 ml). Yet another device may comprise a pre-filled syringe within a housing of the device. The syringe may be fixed within the housing or may be moveable within the housing, for example from a retracted position to an operation extended position.

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 17 and 29 Gauge.

The delivery devices described herein can also include one or more automated functions. For example, one or more of combining the needle and cartridge, needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of combining the needle and cartridge, needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
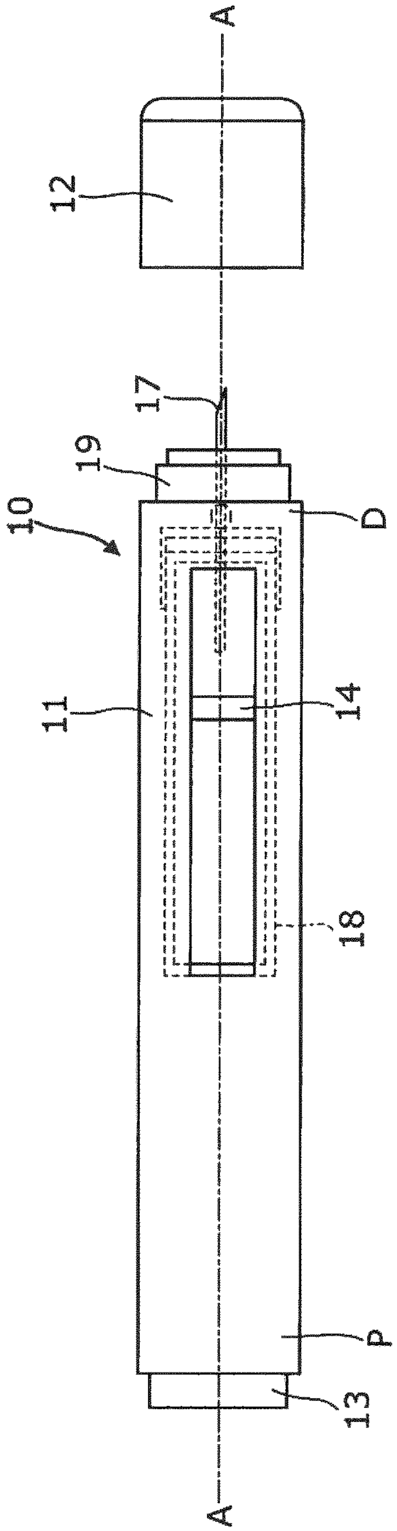
FIG. 1B is a schematic side view of the injector device of FIG. 1A, with the cap removed from the housing.

According to some embodiments of the present disclosure, an exemplary drug delivery device 10 is shown in FIGS. 1A and 1B. Device 10, as described above, is configured to inject a medicament into a patient's body. Device 10 includes a housing 11 which typically contains a cartridge 18 or pre-filled syringe that defines a reservoir containing the medicament to be injected, and the components required to facilitate one or more steps of the delivery process.

The device 10 can also include a cap 12 that can be detachably mounted to the housing 11. Typically, a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated", whereby needle 17 moves relative to housing 11. Such insertion can be triggered by movement of sleeve 19 or by another form of activation, such as, for example, a button 13. As shown in FIGS. 1A and 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location to a more distal location within the reservoir of the cartridge 18 in order to force a medicament from the cartridge 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the cartridge 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the cartridge 18 within housing 11 is moved in a proximal direction relative to housing 11. This proximal movement can be achieved by using a retraction spring (not shown), located in distal region D. A compressed retraction spring, when activated, can supply sufficient force to the cartridge 18 to move it in a proximal direction. Following sufficient retraction, any relative movement between needle 17 and housing 11 can be locked with a locking mechanism. In addition, button 13 or other components of device 10 can be locked as required.

Figure 2:
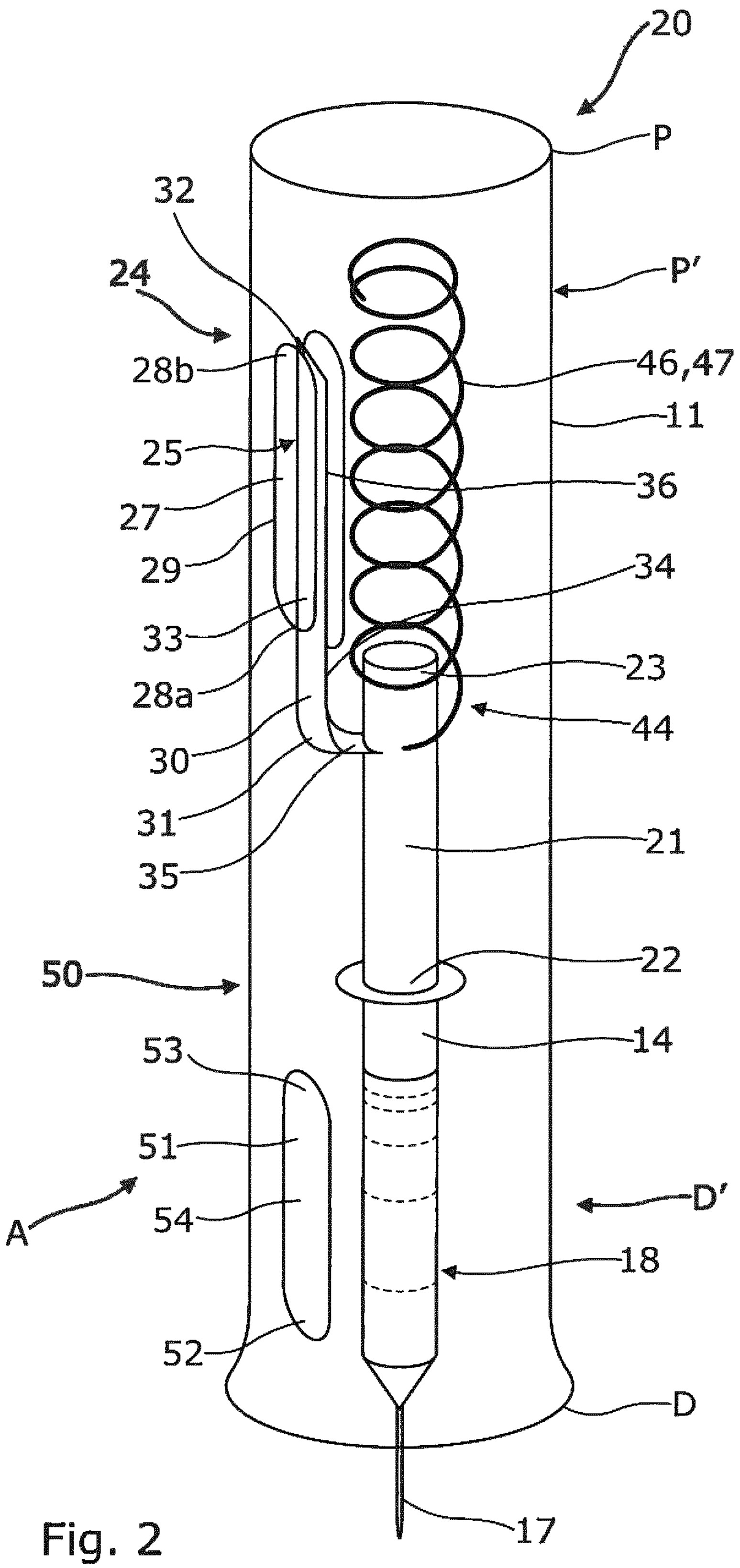
FIG. 2 is a perspective view of an injector device according to the present disclosure in its primed position.

Referring now to FIG. 2, an embodiment of an injector device 20 of the present disclosure is shown. The injector device 20 of the present disclosure is similar to the device 10 described above and so features and components of the device 20 that are the same as the features and components of the above described device 10 will retain the same terminology and reference numbers.

The injector device 20 comprises a housing 11 configured to receive a container of medicament 18, i.e. a cartridge. The container of medicament 18 may refer to a container, as such, for receiving a medicament or a container at least partially filled with medicament. The housing 11 is elongate and comprises a proximal end P and a distal end D. The container of medicament 18 is received in a distal region D' of the housing 11. That is, the container of medicament 18 is located closer to the distal end D of the housing 11 than the proximal end P of the housing 11.

For the purposes of the following description, the distal region D' may be considered to be a part of the housing 11 closer to the distal end D of the housing 11 than the proximal end P of the housing. The proximal region P' of the housing 11 may be considered to be a part of the housing 11 that is closer to the proximal end P of the housing 11 than the distal end D of the housing 11.

Figure 3:
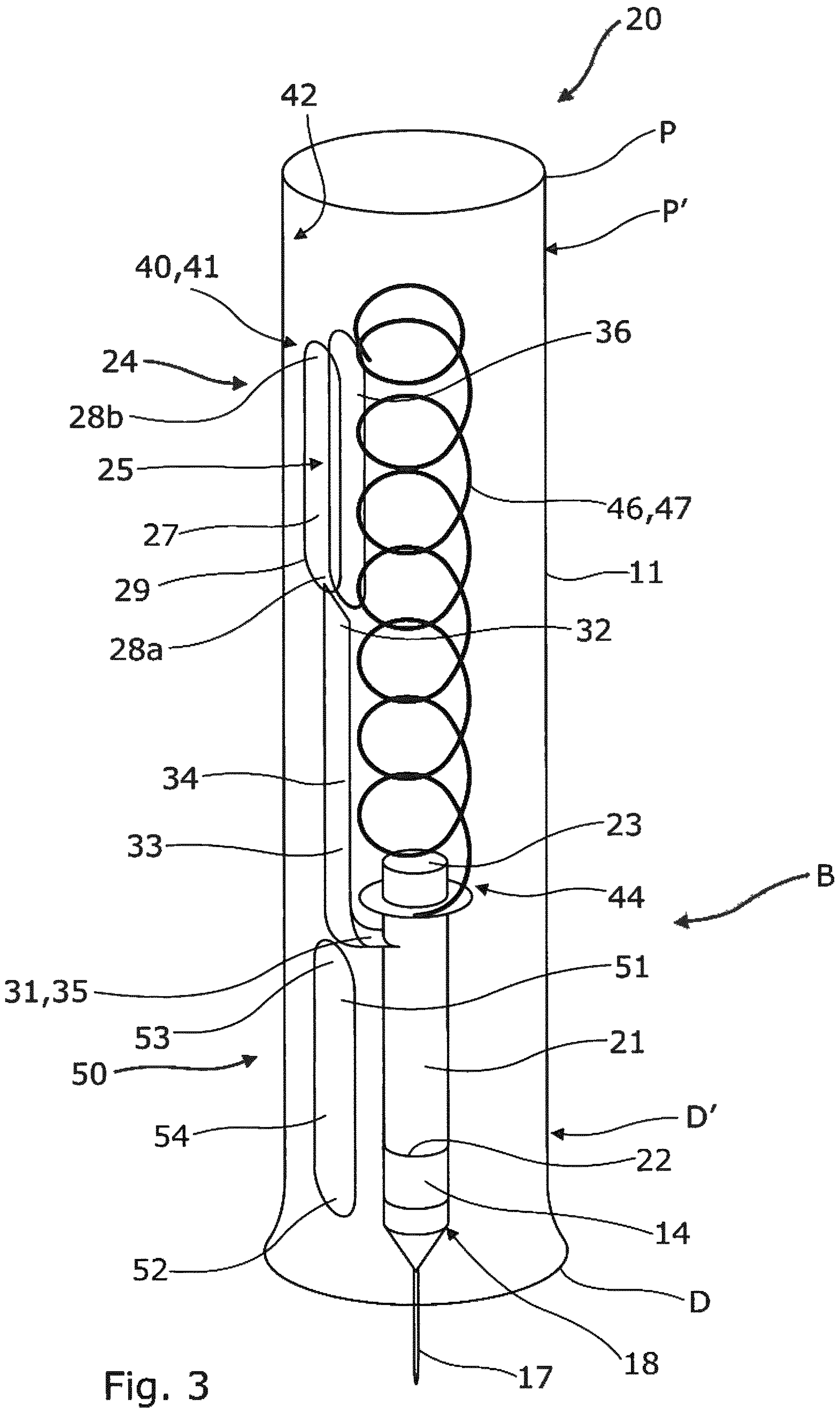
FIG. 3 is a schematic perspective view of the injector device of FIG. 2 in a completed position.

In FIGS. 2 and 3, the housing 11 of the injector device 20 is shown partially transparent in order to show the internal components of the injector device 20 more clearly. For the sake of clarity, some components of the injector device 20 are not shown in FIGS. 2 and 3, such as the cap 12 and the needle sleeve 19, for simplicity.

The injector device 20 further comprises a plunger rod 21 which is moveable longitudinally within the housing 11 between a primed position, shown in FIG. 2, and a completed position, shown in FIG. 3. The plunger rod 21 is located predominantly, if not completely, in the proximal region P' when in its primed position and the plunger rod 21 is located predominantly in the distal region D' when in its completed position. Therefore, the plunger rod 21 is moveable from a proximal region P' of the housing 11 to the distal region D' of the housing 11 during the injection progress. In any case, when the plunger rod 21 is located in its completed position, the plunger rod 21 is located closer to the distal end D of the housing 11 than when the plunger rod 21 is in its primed position.

The injector device 20 further comprises a container of medicament 18. The plunger rod 21 comprises a distal end 22 and a proximal end 23. The container of medicament 18 is received within the housing 11 between the plunger rod 21 and the distal end D of the injector device 20.

The plunger rod 21 comprises a bung 14 located at its distal end 22. The bung 14 is configured to contact the side wall(s) of the container of medicament 18 to form a seal so that the medicament is urged out of the container of medicament 18 and through the needle 17 when the plunger rod 21 is moved longitudinally in the distal direction from the primed position towards the distal position.

The injector device 20 further comprises an indicator 24. The indicator 24 is located in the proximal region P' of the housing 11. The indicator 24 is located in the region of the proximal end P. That is, the indicator 24 is located close to, if not at, the proximal end P of the housing 11. The indicator 24 is configured to provide a user with information associated with the progress of the injection progress dependent upon the longitudinal position of the plunger rod between the primed and completed positions.

Figure 4:
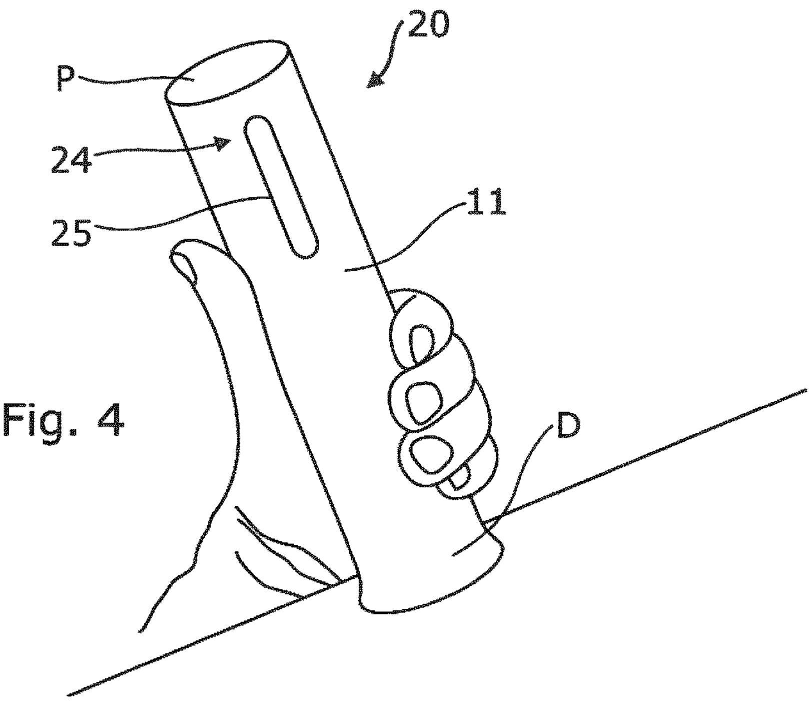
FIG. 4 is a schematic side view of the injector device of FIG. 2 held in use.

In the present embodiment, the indicator 24 comprises a display window 25. The display window 25 is located in a side wall of the housing 11. The display window 25 comprises a distal end **28*a* and a proximal end 28*b*. The display window 25 is located in the proximal region P' of the housing 11. The display window 25 is fully located in the proximal region P' of the housing 11. In the illustrated example, the display window is located close to the proximal end P of the housing 11. That is the proximal end 28*b* of the display window 25 is located next to the proximal end P of the housing 11. Having the display window 25 positioned near the proximal end P of the housing 11 allows a user to grip the injector device 20 closer to the distal end D of the housing 11 which improves the stability of the device 20 during injection due to the user's hand being closer to the injection site. The display window 25 being positioned near the proximal end P of the housing 11 also allows a user to hold the device 20 close to its distal end D whilst still enabling the user to see the indicator 24 and the information associated with the progress of the injection process, as shown in FIG. 4**

In FIGS. 2 and 3, the display window 25 is illustrated as a rectangular aperture 27 in the side wall of the housing 11. The display window 25 has its longitudinal axis extending parallel to the longitudinal axis of the housing 11. The longitudinal length of the display window 25, i.e. the distance between the distal end **28*a* and the proximal end 28*b* is substantially equal to the longitudinal distance that the plunger rod 21** must travel between its primed and completed positions.

It will be understood that the display window 25 could be any other shape, including, but not limited to, triangular, circular, or a curved line. In addition, it will be understood that there may be more than one display window 25 located in the side wall of the housing 11, spaced by a longitudinal gap. The display window 25 may comprise a cover 29 configured to prevent debris from entering the housing 11 of the injection device 20. The cover 29 may be configured such that a user can see through the display window 25 and into the device 20. That is, the cover maybe transparent or translucent.

The indicator 24 further comprises a proximally extending projection 30. The projection 30 comprises a distal end 31 and a proximal end 32. The projection 30 is connected to the plunger rod 21 and extends away from the plunger rod 21 in the proximal direction. The distal end 31 of the projection 30 is connected to the plunger rod 21. The projection 30 is configured to be visible through the display window 25 when the plunger rod 21 is in its primed position, at least.

The projection 30 comprises an outwardly facing surface 33 which is configured to be viewed through the display window 25 when the plunger rod 21 is in its primed position, at least. The outwardly facing surface 33 is located on a longitudinally projecting arm 34 of the projection. The distal end 31 of the projection 30 is connected to the plunger rod 21 in the proximal region of the plunger rod 21, that is, close to the proximal end 23 of the plunger rod 21. The distal end 31 of the projection 30 may comprises a flange 35 which connects the distal end 31 of the arm 34 of the projection 30 to the proximal region of the plunger rod 21.

As illustrated in FIG. 2, the projection 30 extends in the proximal direction such that the majority of the projection 30 is located further from the distal end D of the housing 11 than the proximal end of the plunger rod 21. That is, the proximal end 32 of the arm 34 of the projection 30 is spaced from the proximal end 23 of the plunger rod 21 and is located closer to the proximal end P of the housing 11.

The injector device 20 further comprises an indication element 36. The indication element 36 is located in the same longitudinal position as the display window 25. In some embodiments, the indication element 36 may cover an area slightly larger than the area of the display window 25. The indication element 36 is also located radially inwardly of the display window 25 and the arm 34 of the projection 30 extending from the plunger rod 21. The arm 34 of the projection 30 is located between the display window 25 and the indication element 36. The arm 34 of the projection 30 is configured to obscure a user's view of the indication element 36, when the plunger rod 21 is in its primed position, at least.

The projection 30 is axially coupled to the plunger rod 21. The projection 30 is configured to move between a first indication position A, shown in FIG. 2, and a second indication position B, shown in FIG. 3, when the plunger rod 21 is moved from the primed position, shown in FIG. 2, to the completed position, shown in FIG. 3. Therefore, movement of the plunger rod 21 in the longitudinal direction causes the same amount of movement of the projection 30 in the longitudinal direction. In addition, movement of the projection 30 from the first indicating position A towards the second indicating position B makes a greater portion of the indication element 36 visible through the display window 25.

In one embodiment, when the projection 30 is located in the first indication position A, as shown in FIG. 2, the proximal end 32 of the arm 34 of the projection 30 is located at the proximal end 28*b* of the display window 25. In such an embodiment, most of the indication element 36 may be obscured from view through the display window 25 by the arm 34 of the projection 30 to indicate that the plunger rod 2 is in its primed position. In another embodiment, when the projection 30 is located in the first indication position A, only the arm 34 of the projection 30 may be visible through the display window 25 to indicate that the plunger rod 21 is in its primed position.

In one embodiment, when the projection 30 is located in the second indicating position B, the proximal end 32 of the projection 30 is located at the distal end 28*a* of the display window 25. In such an embodiment, most of the indication element 36 may be visible through the display window 25. That is, only a small portion of the indication element 36 may be obscured from view through the display window by the arm 34 of the projection 30 when the projection 30 is located in the second indicating position B to indicate that the plunger rod 21 is in its completed position. In another embodiment, when the projection 30 is located in the second indication position B, only the indication element 36 may be visible through the display window 25 to indicate that the plunger rod 21 is in its completed position, as shown in FIG. 3. That is, when the projection 30 is in its second indicating position B, the arm 34 of the projection 30 may not be visible through the display window 25.

In one embodiment, the plunger rod 21 may be constrained to purely longitudinal motion. In such an embodiment, the projection 30 may be integrally formed with the plunger rod 21.

Alternatively, the projection 30 may be fixedly attached to the proximal region of the plunger rod 21. In such embodiments, purely longitudinal motion of the plunger rod 21 from the primed position, shown in FIG. 2, to the completed position, shown in FIG. 3, means that the projection 30 only moves longitudinally and so is always in line with the display window 25 during the injection process.

In another embodiment, the plunger rod 21 may move rotationally during its longitudinal motion from the primed position to the completed position. In such an embodiment, the projection 30 may be rotationally decoupled from the plunger rod 21 such that the projection 30 remains aligned with the display window 25 throughout the injection process. Therefore, any rotational motion of the plunger rod 21 will not cause rotation of the projection 30 and therefore will not remove the projection 30 from the display window 25 through rotational motion.

The projection 30 may be constrained to longitudinal movement by a guide mechanism 40, shown in FIG. 3. The guide mechanism 40 may comprise a guide element 41. The guide element 41 may be located on an inner surface 42 of the housing 11. The guide element 41 may be configured to prevent rotational motion of the projection about the longitudinal axis of the plunger rod 21. In one embodiment, the guide element 41 may protrude inwardly from the inner surface 42 of the housing 11. The guide element 41 may extend longitudinally along the inner surface 42 of the housing 11. The guide element 41 may extend along the periphery of the display window 25 to prevent rotation of the projection 30 away from the display window 25. One guide element 41 may be located on either side of the display window 25 to prevent rotation in both directions about the longitudinal axis.

The guide mechanism 40 may be used to prevent rotation of solely the projection 30 or of the projection 30 and the plunger rod 21 when the projection is fixedly attached to the plunger rod 21.

In embodiments where the plunger rod 21 and projection 30 are formed separately and then fixed together, the projection 30 may further comprise a connecting element 44. The connecting element 44 is located on the end of the flange 35 opposite to the arm 34. The connecting element 44 may comprise, for example, but not limited to, a snap-fit connection having two arms which fit around the proximal region of the plunger rod 21 or an annular ring which locates in a groove on the plunger rod 21. These types of connecting elements 44 allow for rotation of the plunger rod 21 relative to the projection 30.

In one embodiment, the projection 30 may comprise an annular element (not shown), instead of a longitudinally extending arm 34. The annular element may extend up to 360 degrees around the longitudinal axis so that any rotation of the projection 30 relative to the plunger rod 21 does not remove the projection 30 from the display window 25.

The outward facing arm 34 of the projection 30 and the indication element 36 comprise different indicia configured to help a user determined the progress of the injection process at any time. The outward facing arm 34 of the projection 30 comprises a first indicia and the indication element 36 comprises a second indicia, different to the first indicia. The indicia may be, for example, but not limited to, one or more colours, colour gradients, patterns, images, or number scale, etc.

The injector device 20 may be mechanically driven. The indicator 24 may be a mechanical indicator. For example, the injector device 20 shown in FIGS. 2 and 3 comprises a biasing element 46. In the present embodiment, the biasing element is a helical spring 47. When the injector device 20 is actuated and the plunger rod 21 is free to move distally, the biasing element 46 urges the plunger rod 21 towards the distal end D of the housing 11. The spring 47 may abut the flange 35 of the projection 30 or the proximal end 23 of the plunger rod 21 in order to urge the plunger rod 21 towards its completed position. The longitudinal motion of the plunger rod 21 in the distal direction also causes longitudinal motion of the projection 30 in the distal direction and causes the proximal end 32 of the arm 34 of the projection to move from the proximal end of the display window 25 in the distal direction towards the distal end 28*a* of the display window 25 to reveal the indication element 36. As the spring 47 extends further, the proximal end 32 of the projection 30 moves closer to the distal end 28*a* of the display window 25 and reveals more of the indication element 36.

In one embodiment, the housing 11 of the injector device 20 may further comprise a second indicator 50. The second indicator 50 comprises a second display window 51 having a distal end 52 and a proximal end 53. The second display window it located at the distal region D' of the housing 11. That is the second indicator is located proximate to the distal end D of the housing 11. The second display window 51 may also comprise a cover 54. When the plunger rod 21 is in its primed position and a container of medicament 18 is received in the housing 11, the container of medicament 18 is visible through the second display window 51.

As the plunger rod 21 is moved longitudinally towards the completed position, the distal end 22 of the plunger rod 21 moved through the second display window 51. When the plunger rod 21 is moved into its completed position, the distal end 22 of the plunger rod 21 may be located at the distal end of the second display window 51.

The plunger rod 21, projection 30, and indication element 36 may comprise indicia. In one embodiment, the plunger rod 21 and projection 30 may comprise a first indicia and the indication element 36 may comprise a second indicia, different to the first indicia. In such an arrangement, the indicia will indicate to a user how far the plunger rod 21 has travelled by the movement of the first indicia through the first and second display windows 25, 51 and by the increasing size of the area of the indication element 36 as the plunger rod 21 is moved from its primed position to its completed position.

In an alternative embodiment, the plunger rod 21 and the indication element 36 may comprise a first indicia and the projection 30 may comprise a second indicia, different to the first indicia. The second indicia on the projection 30 is similar to the appearance of the medicament in the container of medicament 18. In such an arrangement, the progress of the injection process will be apparent to a user as the second indicia signifies how far the plunger rod has left to travel and a first indicia signifies how close to the end of the process the plunger rod 21 is.

Figure 5:
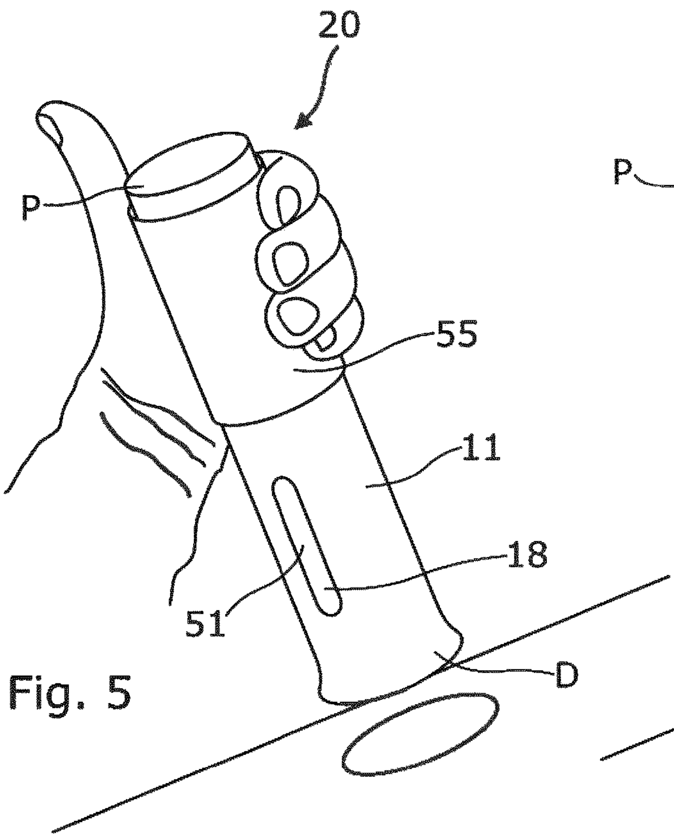
FIG. 5 is a schematic side view of the injector device of FIG. 2 comprising an external sleeve.
Figure 6:
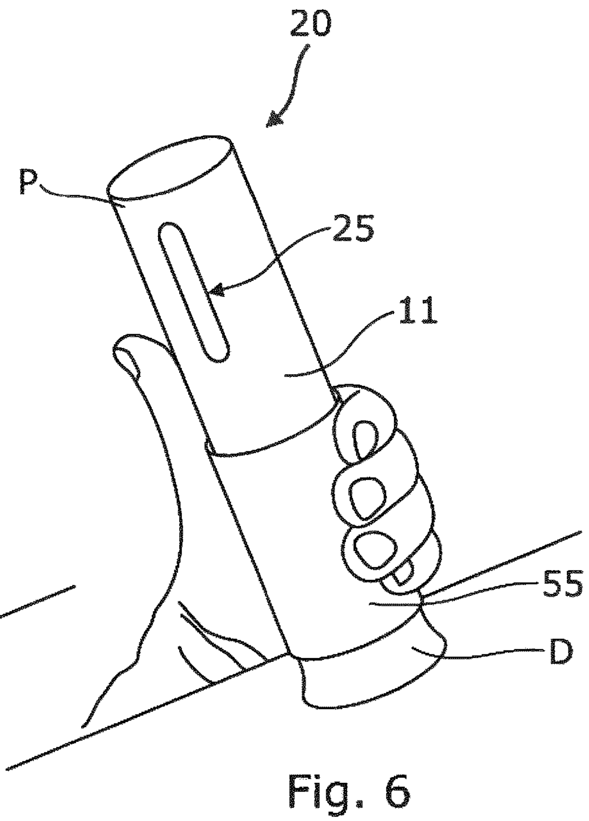
FIG. 6 is a schematic side view of the injector device of FIG. 5 held during an injection process.

Referring briefly to FIGS. 5 and 6, the injector device 20 may further comprise an external sleeve 55. The external sleeve 55 is configured to extend around the housing 11. Furthermore, the external sleeve 55 is configured to be moveable longitudinally from a first position at the proximal end P of the housing 11, shown in FIG. 5, to a second position at the distal end D of the housing 11, shown in FIG. 6.

Referring to FIG. 5, when the external sleeve 55 is in its first position, the second display window 51 is visible and the container of medicament 18 within the housing 11, whilst the first display window 25 is hidden behind the external sleeve. Now, referring to FIG. 6, when the external sleeve 55 is in its second position, the second display window 51 is hidden and the first display window 25 is visible.

The external sleeve 55 is moveable by a user when they grip the injector device 20. The force required to move the external sleeve 55 is less than the force required to retract the needle sleeve 19 into the housing 11 so that when a user pushes the distal end D of the device 20 into their body, the external sleeve moves longitudinally to the distal end of the housing 11 before the needle sleeve 19 is retracted. This ensures that a user holds the injector device 20 close to the distal end D of the housing 11 to improve stability of the device 20 during the injection process.

Figure 7:
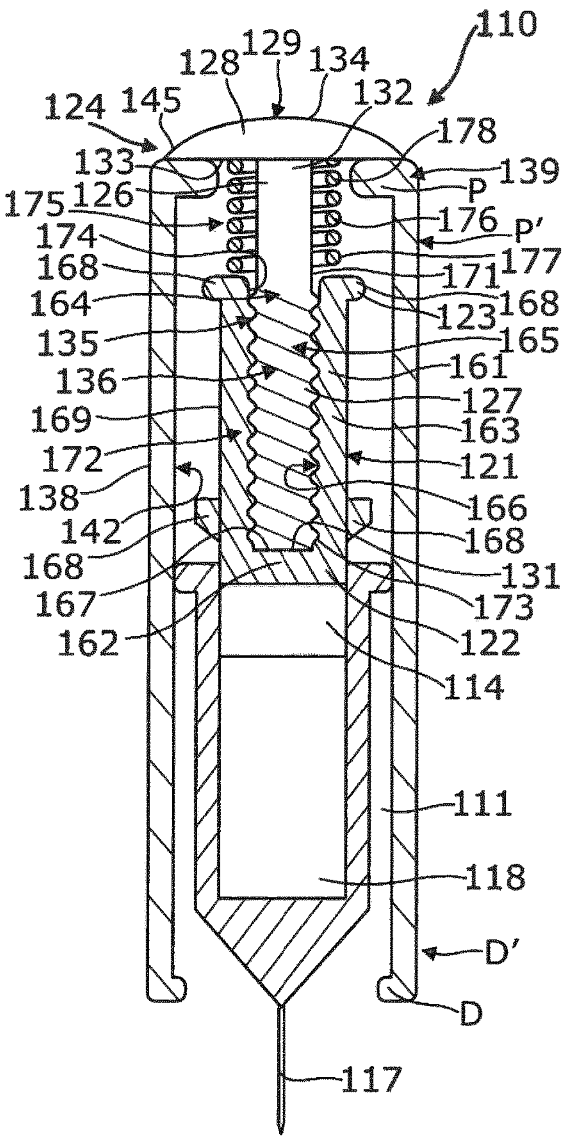
FIG. 7 is a schematic cross-sectional view of an injector device according to the present disclosure in a primed position.
Figure 8:
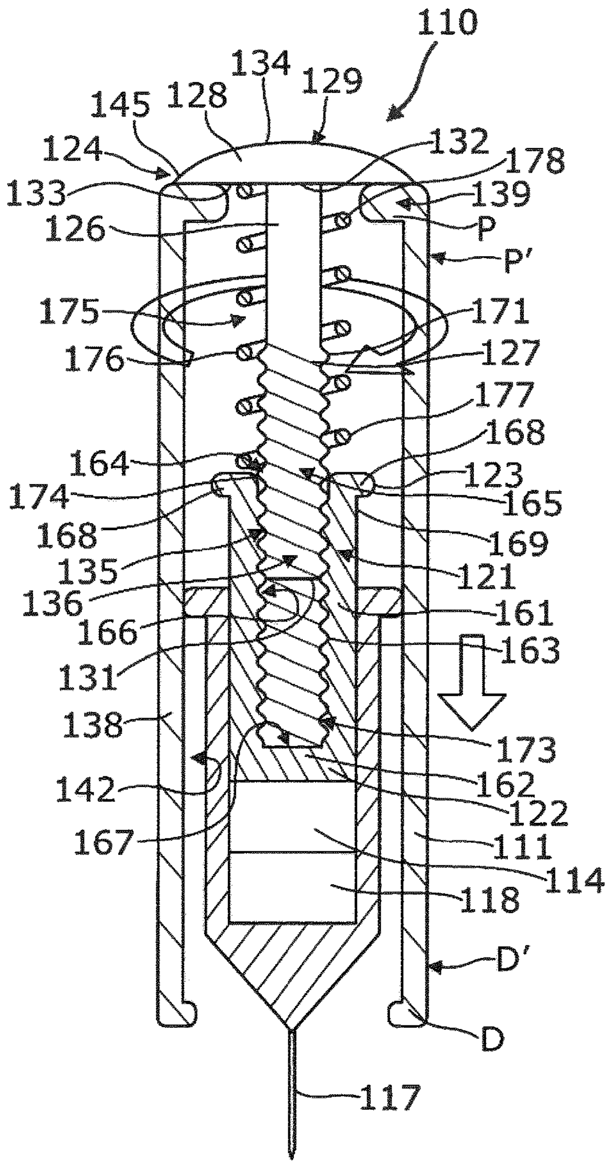
FIG. 8 is a schematic cross-sectional view of the injector device of FIG. 7, showing a plunger rod moved towards the completed position.

Referring now to FIGS. 7 and 8, an embodiment of an injector device 110 of the present disclosure is shown. The injector device 110 of the present disclosure is similar to the injector device 10 described above and so features and components of the device 110 that are the same as features and components of the above described device 10 will retain the same terminology and corresponding reference numbers.

The injector device 110 comprises a housing 111 configured to receive a container of medicament 118, i.e. a cartridge. The container of medicament 18 may refer to a container, as such, for receiving a medicament or a container at least partially filled with medicament. The housing 111 is elongate and comprises a proximal end P and a distal end D. The container of medicament 118 is received in a distal region D' of the housing 111. That is, the container of medicament 118 is located closer to the distal end D of the housing 111 than the proximal end P of the housing 111.

For the purposes of the following description, the distal region D' may be considered to be a part of the housing 111 closer to the distal end D of the housing 111 than the proximal end P of the housing 111. The proximal region P' of the housing 111 may be considered to be a part of the housing 111 that is closer to the proximal end P of the housing 111 than the distal end D of the housing 111.

In FIGS. 7 to 10 the housing 111 of the injector device 110 is shown in schematic cross-sectional drawings in order to show internal components of the injector device 110 more clearly. For the sake of clarity some components of the injector device 110 are not shown in the FIGS. 7 to 10, such as the cap 12 and the needle sleeve 19, for simplicity.

The injector device 110 further comprises a plunger rod 121 which is moveable longitudinally within the housing 111 between a primed position, shown in FIG. 7, and a completed position, the plunger rod 121 having almost reached this position in FIG. 8. The plunger rod 121 is located predominantly, if not completely, in the proximal region P' when in its primed position and the plunger rod 121 is located predominantly, if not completely, in the distal region D' when in its completed position. Therefore, the plunger rod 121 is moveable from a proximal region P' of the housing 111 to the distal region D' of the housing 111 during the injection progress. In any case, when the plunger rod 121 is located in its completed position, the plunger rod 121 is located closer to the distal end D of the housing 111 than when the plunger rod 121 is in its primed position.

The injector device 110 further comprises a container of medicament 118. The plunger rod comprises a distal end 122 and a proximal end 123. The container of medicament 118 is received within the housing 111 between the plunger rod 121 and the distal end D of the injector device 110.

The plunger rod 121 comprises a bung 114 located at its distal end 122. The bung 114 is configured to contact the side wall(s) of the container of medicament 118 to form a seal so that the medicament is urged out of the container of medicament 118 and through the needle 117 when the plunger rod 121 is moved longitudinally in the distal direction from the primed position towards the distal position.

The injector device 110 further comprises an indicator 124. The indicator 124 is located in the proximal region P' of the housing 111. The indicator 124 is located in the region of the proximal end P. That is, the indicator 124 is located close to, if not at, the proximal end P of the housing 111. The indicator 124 is configured to provide a user with information associated with progress of the injection process dependent upon the longitudinal position of the plunger rod 121 between the primed and completed positions.

The indicator 124 of the injector device 110 comprises a spindle 126. The spindle 126 comprises a shaft 127 and a dial 128. The dial 128 is configured to rotate to provide a user with information associated with the progress of the injection process dependent upon the longitudinal position of the plunger rod 121. The dial 128 comprises a display surface 129. The display surface 129 of the dial 128 provides the information associated with the progress of the injection process. The dial 128 is fixedly attached to the shaft 127 such that rotational motion of the shaft 127 causes the dial 128 rotate.

As shown in FIGS. 7 and 8, the shaft 127 of the spindle 126 comprises a distal end 131 and a proximal end 132. The shaft 127 is fixedly attached to the dial 128 at its proximal end 132. In the present embodiment, the dial 128 has a larger diameter than the shaft 127 of the spindle 126. The larger diameter of the dial 128 allows for a larger display surface 129 for providing information associated with the progress of the injection process to the user. The dial 128 comprises a distal surface 133 and an opposing proximal surface 134. The proximal surface 134 of the dial 128 faces outwards of the device 110. In the present embodiment, the proximal surface 134 is the display surface 129. That is, the proximal surface 134 provides the information associated with the progress of the injection process.

The plunger rod 121 comprises a first threaded arrangement 135 and the shaft 127 of the spindle 126 comprises a second threaded arrangement 136. The second threaded arrangement 136 on the shaft 127 is configured to engage with the first threaded arrangement 135 on the plunger rod 121. The engagement between the threaded arrangements 135, 136 on the plunger rod 121 and shaft 127 of the spindle 126 is configured such that longitudinal movement of the plunger rod 121 from the primed position towards the completed position causes the shaft 127 and therefore the dial 128 to rotate to provide a user with information associated with the progress of the injection process, as will be described in more detail hereinafter.

The spindle 126 is constrained from movement in the longitudinal direction. That is, the spindle 126 is prevented from moving longitudinally. In some embodiments, the spindle 126 is prevented from moving in the longitudinal direction by the housing 111. There are many ways in which the housing 111 can be configured to prevent longitudinal movement of the spindle 126.

For example, in one embodiment shown in FIGS. 7 and 8, the dial 128 contacts the proximal end P of the housing 111. That is, the dial 128 is located at the proximate end of the housing 111 such that distal surface 133 of the dial 128 contacts the proximal end of the housing 111.

The housing 111 comprises a side wall 138 which extends longitudinally and at the proximal end P of the housing 111, the side wall 138 comprises an end wall or surface 139. In the present embodiment, the end surface 139 is annular when viewed from the proximal end P of the housing 111. However, in some embodiments, the end wall 139 may comprise an end plate which extends across the proximal end P of the housing 111.

Furthermore, the dial 128 is positioned such that the distal surface 133 of the dial 128 contacts the end surface 139 at the proximal end of the housing 111. Thus, when the plunger rod 121 is moved longitudinally from the primed position towards the completed position, the end surface 139 of the housing 111 prevents the spindle 126 from moving longitudinally towards the completed position by acting against the distal surface 133 of the dial 128. In an embodiment where the dial 128 is located at the proximal end of the housing 111, the proximal surface 134 of the dial 128 is the proximal most end of the device 110.

Other example configurations to prevent longitudinal movement of the spindle 126 include an inner surface 142 of the housing 111 comprising a groove (not shown) (143) into which a projection (not shown) (144) extending from the shaft 127 or a side face 145 of the dial 128 locates. Such a groove can prevent longitudinal movement of the spindle 126 towards and away from the completed position. Alternatively, a projection 144 may extend from the inner surface 142 of the housing 111 into a groove 143 located in the shaft 127 of the spindle 126, shown in FIG. 10, or in a side face 141 of the dial 128. In some embodiments, the projection may be formed by an end plate which forms the end surface 139 of the housing 111.

Figure 9:
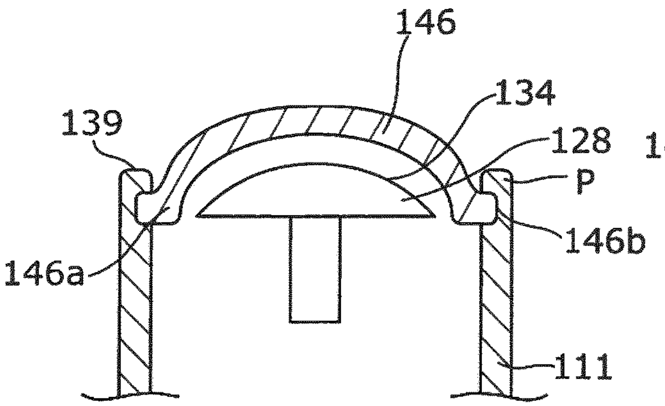
FIG. 9 is a schematic cross-sectional view of an alternative arrangement of a dial at the proximal end of the injector device of FIG. 7.

In an alternative embodiment as shown in FIG. 9, the dial 128 may be located inside the housing 111 such that the proximal surface 134 of the dial 128 faces out of the housing 111 to provide a user with information associated with the progress of the injection process. In such an embodiment, the dial 128 is located within the housing 111 such that the proximal surface 134 of the dial 128 does not extend beyond the plane of the proximal end P of the housing 111. That is, the proximal surface 134 of the dial 128 does not extend beyond the end surface 139 of the housing 111.

The housing 111 further comprises a cover 146. The cover 146 extends over the proximal surface 134 of the dial 128. The cover 146 may also extend over the proximal end P of the housing 111. The cover 146 may comprise a peripheral protrusion 146*a* which is configured to be located in a groove 146*b* on the inner surface 142 of the housing 111. In some embodiments, the cover 146 may not extend beyond the plane of the proximal end P of the housing 111, i.e. the cover 146 does not extend beyond the end surface 139 o the housing 111. In other embodiments, the cover 146 may form the proximal most end of the injector device 110.

The cover 146 is configured such that the dial 128 can provide visual feedback to a user associated with the progress of the injection process. The cover 146 may be transparent, or at least translucent, to allow a user to see the dial 128 below. In some embodiments, only a part of the cover may be configured to allow a user to see the dial 128.

The dials 128 shown in FIGS. 7 to 9 may be configured in a variety of different ways in order to provide visual feedback to the user associated with the progress of the injection process. The proximal surface 134 of the dial 128 may be curved such that the proximal surface is dome shaped or in alternative embodiments, the proximal surface 134 of the dial 128 may be flat. Furthermore, the proximal surface 134 of the dial 128 may be uninterrupted. That is, the proximal surface 134 may be without holes or indents, etc. In such an embodiment, the proximal surface 134 of the dial 128 may comprise indicia configured to line up with indicia on the proximate end of the side wall 138 of the housing 111.

For example, one of the proximate surface 134 and the side wall 138 may comprise an arrow pointing towards the periphery of the dial 128 and the other of the proximate surface 134 and the side wall 138 may comprise indicia which provide information associated with the progress of the injection process by way of, for example, but not limited to, a number scale, colour gradient, or words representing events that occur during the injection process.

Figure 11:
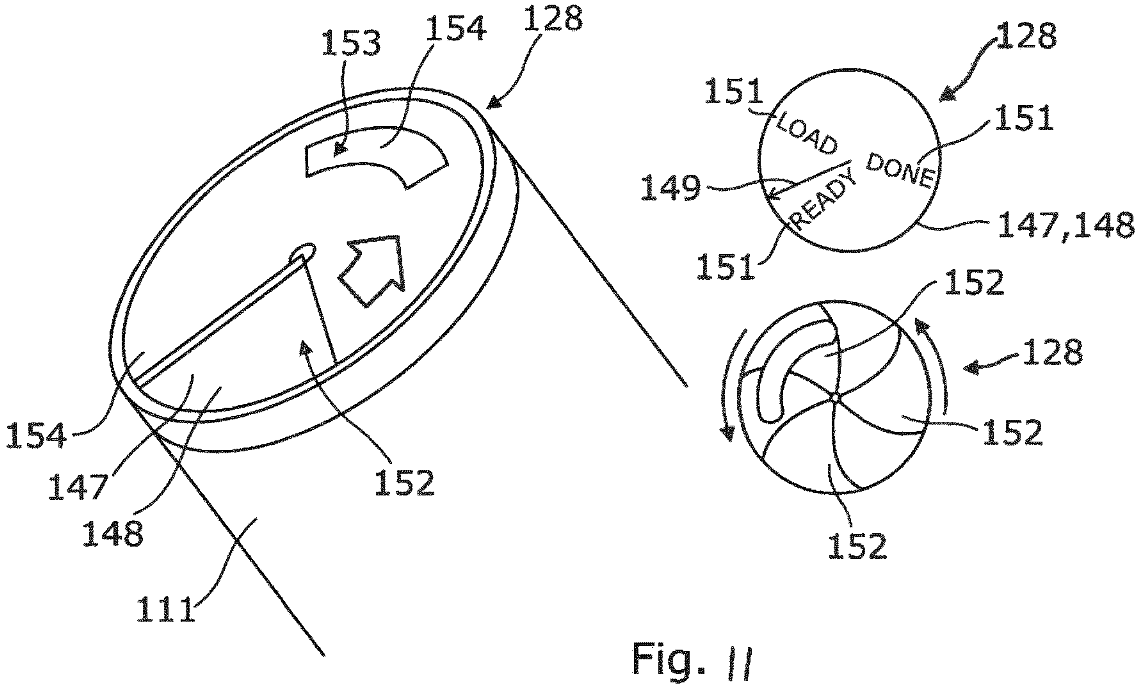
FIG. 11 is a collection of embodiments of indicia on the dial arrangement of the injector device of FIG. 7.

Referring briefly to FIG. 11, yet further exemplary embodiments of the dial 128 are shown. Referring to the embodiment shown in the top right of FIG. 11, the dial 128 may be at least partially transparent. That is, the whole dial 128 may be transparent, or at least translucent, such that a user may see through the dial 128. Alternatively, only a part of the dial 128 may be transparent or translucent. The injector device 110 may further comprises a display plate 147 located in the housing 111 distal of the dial 128. The display plate 147 may comprise indicia on its proximate surface 148, i.e. the surface facing outwards of the injector device 110 and towards the dial 128. In the example shown, one of the dial 128 and the proximate surface 148 of the display plate 147 comprises an arrow 149 and the other of the dial 128 and the proximate surface 148 comprises indicia 151 in the form of words representing events that occur during the injection process. As the plunger rod 121 is moved longitudinally towards its completed position, the dial 128 will rotate and the event to which the arrow 149 points will change to provide the user with information associated with the progress of the injection process.

It will be appreciated that the shaft 127 of the spindle 126 may pass through a central hole in the display plate 147. Furthermore, it will be appreciated that it may be the display plate 147 of the housing 111 which comprises a groove 143 or projection 144 to interact with the shaft 127 of the spindle 126 to prevent longitudinal movement of the spindle 126 during the injection process. It will be further appreciated that the display plate 147 may form the end surface 139 of the housing 111 in some embodiments.

Referring briefly to the embodiment shown on the left of FIG. 11, the dial 128 may comprise a cut-out 152. The cut-out 152 extends through the dial 128 from the proximal surface 134 to the distal surface 133 and enables a user to see the display plate 147 below the dial 128. The cut-out 152 may have, for example, but not limited to, sector shaped. The dial 128 may also comprise a display window 153. The display window 153 is similar to the cut-out in that it extends through the dial 128 from the proximal surface 134 to distal surface 133 to enable a user to see the display plate 147 below the dial 128. The display window 153 may be, for example, but not limited to semi-circular or crescent shaped. However, the cut-out 152 and display window 153 may be at different radial and angular positions in the dial 128 and may be used to provide different information about the progress of the injection process. Referring briefly to the embodiment shown in the bottom right of FIG. 11, it can be seen that multiple cut-outs 152 can be formed in the dial 128.

Both the cut-outs 152 and the display windows 153 may comprise a cover 154 configured to be placed in the cut-out 152 or display window 153 to prevent debris entering the housing 111 of the injector device 110. The cover 154 may be transparent, or at least translucent, in order to enable a user to see through the cover 154 to the indicia located on the proximate surface 148 of the display plate 147. The cover 154 may be formed by a transparent or translucent portion of the dial 128 rather than being an insert into a cut-out 152 or display window 153.

In the above embodiments, as the dial 128 rotates relative to the display plate 147, the cut-outs 152 and/or windows 153 are moved over the proximal surface 148 of the display plate 147 such that as the rotational position of the cut-out 152 and/or display window 153 changes, so does the indicia on the proximal surface 148 of the display plate 147 that is visible through the cut-out 152 and/or display window 153. Therefore, the changing indicia provides visual feedback on the progress of the injection progress.

In the embodiments above, the dial 128 comprises cut-outs 152 and/or display windows 153 to allow a user to see indicia located on the proximate surface 148 of the display plate 147. However, in alternative embodiments, the cover 146 may comprise portions which are transparent, or at least translucent, and the indicia may be located on the proximate surface 134 of the dial 128. Therefore, as the dial 128 rotates relative to the transparent part of the cover 146, the indicia on the proximate surface 134 of the dial 128 pass under the transparent portion of the cover 146 in order to provide a user with information associated with the progress of the injection process.

Figure 10:
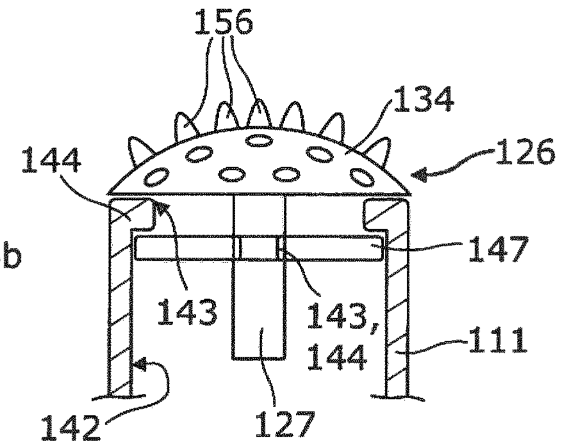
FIG. 10 is a schematic cross-sectional view of an alternative arrangement of a dial at the proximal end of the injector device of FIG. 7.

In some embodiments, the dial 128 may be configured to provide tactile feedback to a user associated with the progress of the injection process, instead of visual feedback. An example of such an embodiment is illustrated in FIG. 10. In FIG. 10, the proximal surface 134 of the dial 128 comprises a surface formation 156 configured to provide tactile feedback to a user associated with the progress of the injection process. The surface formation 156 may be formed by, for example, but not limited to, one or more protrusions, one or more indents, or surface roughness.

In yet a further embodiment of the injector device 110, the dial 128 may be housed inside the housing 111. The housing 111 may comprise a display window (158) in its side wall 138 through which the side face 145 of the dial 128 can be seen. The side face 145 of the dial 128 may comprise indicia configured to provide visual feedback to a user associated with the progress of the injection process.

Referring back to FIGS. 7 and 8, the plunger rod 121 is shown in threaded engagement with the shaft 127 of the spindle 126. In the present embodiment the first threaded arrangement 135 on the plunger rod 121 faces inwardly. That is, in the present embodiment, the plunger rod 121 comprises a hollow tubular housing 161. The tubular housing 161 comprises a distal wall 162 and a longitudinally extending side wall 163. In the present embodiment, the housing 161 is cylindrical and so the side wall 163 is annular when viewed from the proximal end P of the housing 111. The tubular housing 161 comprises an open proximal end 164 and an internal cavity 165. The internal cavity 165 is defined by an inner surface 166 of the side wall 163 and an inner surface 167 of the distal wall 162. The first threaded arrangement 135 on the plunger rod 121 is formed on the inner surface 166 of the side wall 163 of the plunger rod 121.

The plunger rod 121 is constrained to longitudinal movement. That is, plunger rod 121 can move in the longitudinal direction but is prevented from rotating about the longitudinal axis. The plunger rod 121 comprises a projection 168 configured to be located in a groove on the inner surface 142 of the housing 111. The projection 168 extends radially outward from an outer surface 169 of the plunger rod 121. The groove in the inner surface 142 of the housing 111 extends longitudinally and over a distance which is at least equal to the distance that the plunger rod 121 must travel between primed and completed positions. The side walls of the groove abut the projection 168 of the plunger rod 121 to prevent rotation of the plunger rod 121 relative to the housing 111.

The cavity 165 formed in the plunger rod 121 is configured to at least partially receive the shaft 127 of the spindle 126. When the plunger rod 121 is in its primed position, the distal end 131 of the shaft 127 abuts the inner surface 167 of the distal wall 162, i.e. the proximal surface of the plunger rod 121. The shaft 127 of the spindle 126 comprises a second threaded arrangement 136 on an outer surface 171 of the shaft 127. The second threaded arrangement 136 on the outer surface 171 of the shaft 127 of the spindle 126 is configured to threadingly engage the first threaded arrangement 135 on the inner surface 166 of the plunger rod 121.

In the embodiment shown in FIG. 7 and FIG. 8, the shaft 127 of the spindle 126 is located inside the plunger rod 121. However, it will be understood that in an alternative embodiment, the shaft 127 of the spindle 126 maybe located outside of the plunger rod 121. In such an embodiment, the first threaded arrangement 135 may be located on the outer surface 169 of the plunger rod 121 and the second threaded arrangement 136 would be located on an inner surface of the shaft 127.

In the present embodiment, the first threaded arrangement 135 on the plunger rod 121 comprises a continuous threaded arrangement. That is, the continuous threaded arrangement comprises a continuous thread 172. The continuous threaded arrangement extends from a distal end 173 of the inner surface 166 of the plunger rod 121 to a proximal end 174 of the inner surface 166 of the plunger rod 121. That is, the continuous first threaded arrangement 135 extends along the length of the inner surface 166 of the plunger rod 121. Similarly, the second threaded arrangement 136 on the shaft 127 of the spindle 126 comprises a continuous threaded arrangement. The continuous threaded arrangement extends from the distal end 131 of the shaft 127 towards the proximal end 132 of the shaft 127. In the present embodiment, the second threaded arrangement 136 only extends along the shaft 127 by a distance equal to the length of the inner surface 166 of the plunger rod 121. Therefore, the first and second threaded arrangements 135, 136 are in contact throughout the longitudinal movement of the plunger rod 121 between the primed and completed positions.

The inner surface 166 of the side wall 163 of the plunger rod 121 determines the maximum longitudinal distance of travel between the primed position and the completed position of the plunger rod 121. This is necessary because once the plunger rod 121 and spindle 126 are no longer in threading engagement, the dial 128 cannot provide accurate information about the progress of the injection process. The continuous thread on the plunger rod 121 and/or the shaft 127 of the spindle 126 is configured to ensure that the spindle 126 is constantly rotated as the plunger rod 121 is moved axially to provide constant feedback on the progress of the injection process.

In some embodiments, the longitudinal length of the continuous thread on one of the plunger rod 121 and the shaft 127 of the spindle 126 is equal to the longitudinal distance between the primed position of the plunger rod 121 and the completed position of the plunger rod 121. This enables the dial 128 of the spindle 126 to provide feedback on the progress of the injection process dependent upon the position of the plunger rod 121 at any stage between the primed position and the completed position.

In other embodiments, the longitudinal length of the continuous thread on one of the plunger rod 121 and the shaft 127 of the spindle 126 is greater than the longitudinal distance between the primed position of the plunger rod 121 and the completed position of the plunger rod 121. This enables the dial 128 of the spindle 126 to provide feedback on the progress of the injection process dependent upon the position of the plunger rod 121 at stages before the plunger rod 121 is moved into its primed position and/or after the plunger rod 121 has been moved into its completed position.

For example, the plunger rod 121 may have a loading position proximal to the primed position in which the plunger rod 121 is held until a container of medicament 118 is loaded into the housing 111. The plunger rod 121 may then be moved distally from a loading position into the primed position in which the bung 114 is in contact with the proximal end of the container of medicament 118.

It can be seen in FIGS. 7 and 8 that the injector device 110 further comprises a biasing element 175. In the embodiments shown, the biasing element 175 is a helical spring 176. However, it will be clear to a person skilled in the art that any other type of biasing member 175 could be used. The helical spring 176 is located such that its longitudinal axis coincides with the longitudinal axis of the shaft 127 of the spindle 126 and the longitudinal axis of the plunger rod 121. Thus, the helical spring 176 extends about the shaft 127 of the spindle 126. This helps to prevent the spring 176 from bending out alignment with the longitudinal axis when it is compressed.

The helical spring 176 comprises a distal end 177 and a proximal end 178. The distal end 177 of the helical spring 176 is in contact with the proximal end 123 of the plunger rod 121. The proximal end 178 of the helical spring 176 contacts the housing 111 in the proximal region P'. In some embodiments, the proximal end 178 of the helical spring 176 may abut the display plate 147, the inner surface 142 of the housing 111, or a projection extending from the inner surface 142 of the housing 111. When the plunger rod 121 is in its primed position, the biasing member 175 is in a higher state of compression than when the plunger rod 121 is in its completed position.

When the injector device 110 is actuated, a locking element which prevents longitudinal movement of the plunger rod 121 is released and the biasing member 175 extends from its compressed state. The proximal end 178 of the helical spring 176 is attached to the housing 111 which is fixed and so the extension of the spring 176 urges the distal end 177 of the spring 176 and therefore the plunger rod 121 distally in the longitudinal direction. Movement of the plunger rod 121 in the distal direction is constrained to longitudinal movement due to the location of a projection 168 from the plunger rod 121 in a groove in the inner surface 142 of the housing 111.

The longitudinal movement of the plunger rod 121 causes the first threaded arrangement 135 to move distally. Due to the spindle 126 being prevented from movement in the longitudinal direction, the longitudinal distal movement of the first threaded arrangement 135 causes the second threaded arrangement 136 to slip against the first threaded arrangement 135. This caused the shaft 127 of the spindle 126 and therefore the dial 128 to rotate. The rotation of the dial 128 provides feedback to the user of the progress of the injection progress.

Figure 12:
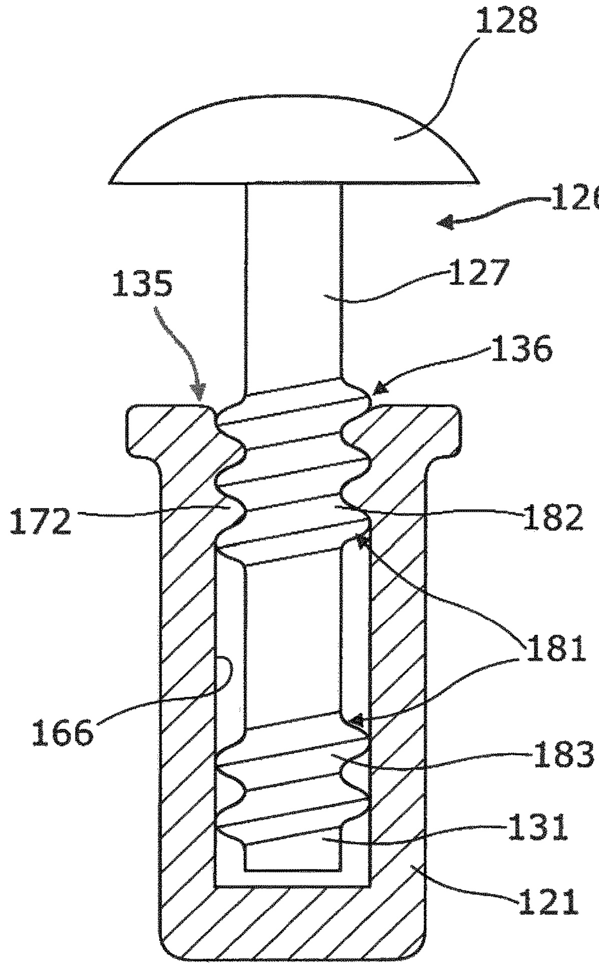
FIG. 12 is a schematic cross-sectional view of an alternative threaded engagement of the injector device of FIG. 7.

Referring briefly to FIG. 12 another embodiment of the threaded arrangements can be seen. In the alternative embodiment, the threaded arrangement comprises a non-continuous thread 181 on one of the plunger rod 121 and the shaft 127 of the spindle 126. In FIG. 12, the first threaded arrangement 135 on the inner surface 166 of the plunger rod 121 is a continuous thread 172. However, the continuous thread 172 only extends over a small longitudinal distance at the proximal end of the plunger rod 121. The second threaded arrangement 136 on the shaft 127 of the spindle 126 comprises the non-continuous thread 181. The non-continuous thread 181 comprises a proximal portion 182 and a distal portion 183.

Therefore, upon longitudinal movement of the plunger rod 121, the continuous first threaded arrangement 135 on the plunger rod 121 engages the proximal portion 182 of the non-continuous second threaded arrangement 136 to rotate the dial 128 until the threaded arrangements are no longer in contact. Once the plunger rod 121 and the shaft 127 are not threadingly engaged, further longitudinal movement of the plunger rod 121 does not cause rotation of the dial 128 until the continuous first threaded arrangement 135 on the plunger rod 121 engages the distal portion 183 of the non-continuous second threaded arrangement 136 to rotate the dial 128.

In such an embodiment, the non-continuous thread 181 is configured to provide event specific feedback on the progress of the injection progress. This is shown by the discontinuous rotational movement of the dial 128 as the plunger rod 121 is moved longitudinally from the primed position to the completed position. For example, rotation due to the proximal portion 182 of the non-continuous thread 181 may turn the dial 128 from indicating the container of medicament 118 is loaded to indicating that the plunger rod 121 is in its primed position and rotation due to the distal portion 183 of the non-continuous thread 181 may turn the dial 128 from indicating the plunger rod 121 is in its primed position to indicating that the plunger rod 121 is in its completed position.

In an embodiment in which the first threaded arrangement 135 comprises a non-continuous thread 181 and the second threaded arrangement 136 comprises a continuous thread, the continuous thread may be located on the distal end 131 of the shaft 127.

Furthermore, it will be appreciated that in some embodiments, the continuous thread on one of the plunger rod 121 and the shaft 127 may be replaced with a projection which extends into the continuous or non-continuous thread on the other of the plunger rod 121 and the shaft 127. In these embodiments, the pitch of a thread may be varied along the length of the threaded arrangement. An increase in pitch may result in a lower frictional force with the thread due to the angle of the thread being more closely aligned with the longitudinal direction of movement. Therefore, the pitch of the thread may increase towards the distal end of the shaft 127 in order to reduce the force required from the biasing element 175 to move longitudinally. This helps to overcome the reduced force with which the spring 176 urges the plunger rod 121 as it extends. Alternatively, the pitch may be varied, i.e. decreased, at event specific stages to cause a quicker rotation of the dial 128.

Figure 13:
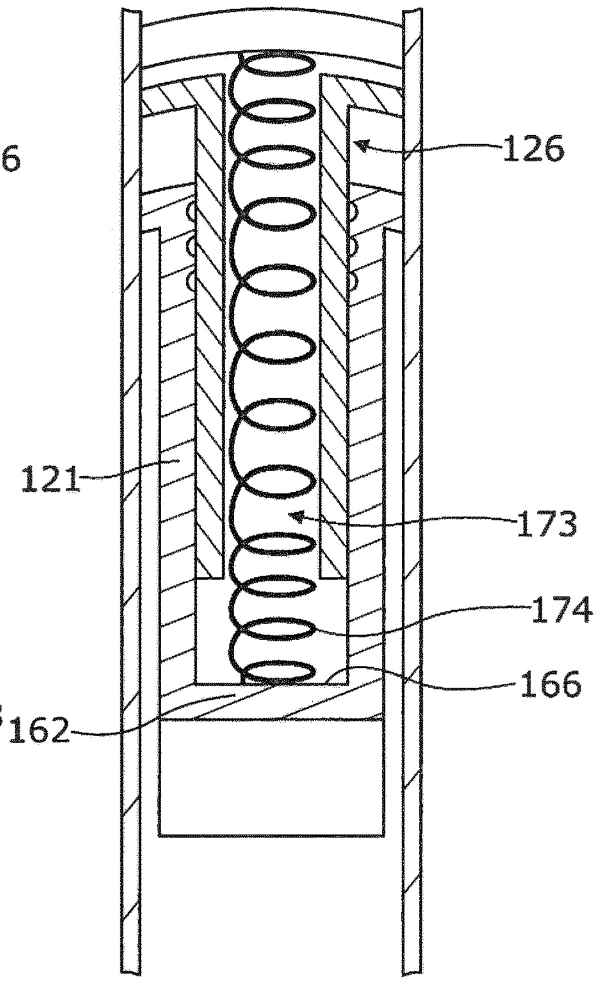
FIG. 13 is a schematic cross-sectional view of an alternative arrangement of a plunger rod and a spindle of the injector device of FIG. 7.

Referring briefly to FIG. 13, it can be seen that in an alternative embodiment, the spindle 126 may be hollow and open-ended. In such an embodiment, the biasing member 175 can be accommodated in the hollow of the spindle 126. Therefore, the distal end 177 of the spring 176 can contact the inner surface 166 of the distal wall 162 of the plunger rod 121.

In some alternative embodiments, the feedback provided by the dial 128 may comprise other types of feedback to the ones discussed above. For example, the feedback provided by the dial 128 may be, but not limited to, an animation, visuals, or motions. The feedback may be intended to comfort a user or receiver of a medicament. In some embodiments, the dial may comprise a display for displaying the feedback. Alternatively, the images may be provided on the surface of the dial.

The feedback may begin when the device is actuated. In some embodiments, the feedback may begin before the plunger rod is moved from the primed position, for example, but not limited to, on removal of the cap or retraction of the needle shield, etc. In some embodiments, the feedback may begin at least 2 seconds before the plunger rod moves. In some examples, the feedback may begin at least 5 seconds before the plunger rod moves.

The feedback may finish when the injection is completed. That is, the feedback may begin when the plunger rod is moved from the primed position and the feedback may finish when the plunger rod is in the completed position. In some embodiments, the feedback may finish after the plunger rod has reach the completed position. The feedback may continue for a given time period after the injection has been completed. For example, the feedback may continue for at least 2 seconds after the injection has been completed. In some examples, the feedback may continue for at least 5 seconds after the injection has been completed.

It will be appreciated by a person skilled in the art that the injector device 20 shown in FIGS. 2 to 6 may incorporate features described with reference to the injector device 110 shown in FIGS. 7 to 13 even though they are not explicitly described in the same embodiment. Furthermore, it will be appreciated by a person skilled in the art that the injector device 110 shown in FIGS. 7 to 13 may incorporate features described with reference to the injector device 20 shown in FIGS. 2 to 6 even though they are not explicitly described in the same embodiment. The embodiments have only been described separately in order to provide clarity in relation to each mechanism and the features shown in FIGS. 2 to 6 and the features shown in FIGS. 7 to 13 could be incorporated into the same injector device.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injector device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injector devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, and Berberine. Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

This specification includes the following clauses:

1. An injector device comprising:

an elongate housing having a proximal end and a distal end, and configured to receive a container of medicament;

a plunger rod moveable longitudinally within the housing between a primed position and a completed position, the plunger rod being configured to be engageable with a container of medicament when received in the housing;

wherein the housing comprises an indicator located in a proximal region of the housing; the indicator being configured to provide a user with information associated with the progress of the injection process dependent upon the longitudinal position of the plunger rod.

2. The injector device according to clause 1, wherein the indicator comprises a spindle, the spindle comprising a shaft and a dial, wherein the dial is configured to rotate to provide a user with information associated with the progress of the injection process dependent upon the longitudinal position of the plunger rod.

3. The injector device according to clause 2, wherein the spindle is constrained from movement in the longitudinal direction and is rotatable relative to the plunger rod.

4. The injector device according to clause 2 or clause 3, wherein the spindle is prevented from moving in the longitudinal direction by the housing.

5. The injector device according to any one of clause 2 to clause 4, wherein the dial is located at the proximal end of the housing such that the distal surface of the dial contacts the proximal end of the housing and the proximal surface of the dial faces outwardly of the device to provide a user with information associated with the progress of the injection process, in use.

6. The injector device according to any one of clause 2 to clause 4, wherein the dial is located inside the housing at the proximal end of the housing such that a proximal surface of the dial faces out of the housing to provide a user with information associated with the progress of the injection process.

7. The injector device according to any one of clause 2 to clause 6, wherein the proximal surface of the dial comprises a surface formation configured to provide tactile feedback to a user associated with the progress of the injection progress.

8. The injector device according to clause 6, wherein the housing comprises a cover extending from the proximal end of the housing and over the proximal surface of the dial, the cover being configured such that the dial can provide visual feedback to a user associated with the progress of the injection progress.

9. The injector device according to any one of clause 2 to clause 4, wherein the dial is housed inside the proximal end of the housing, and the housing further comprises a display window in its side face through which a side face of the dial can be seen, the side face of the dial comprising indicia configured to provide visual feedback to a user associated with the progress of the injection progress.

10. The injector device according to any one of clause 2 to clause 9, wherein the shaft of the spindle comprises a threaded arrangement configured to engage with a threaded arrangement on the plunger rod such that longitudinal movement of the plunger rod from the primed position towards the completed position is configured to cause the dial of the spindle to rotate.

11. The injector device according to clause 10, wherein the threaded arrangement comprises a continuous thread on at least one of the plunger rod and the shaft of the spindle, the continuous thread being configured to provide constant feedback on the progress of the injection process.

12. The injector device according to clause 10 or clause 11, wherein the threaded arrangement comprises a non-continuous thread on one of the plunger rod and the shaft of the spindle, the non-continuous thread being configured to provide event specific feedback on the progress of the injection process.

13. The injector device according to clause 11 or clause 12, wherein the plunger rod is hollow and comprises an open proximal end configured to receive the shaft of the spindle, the plunger rod comprising a thread on its inner surface and the shaft comprising a thread on its outer surface.

14. An injector device according to any one of the preceding clauses, further comprising a container of medicament received within the housing between the plunger rod and the distal end of the injector device.

15. A method of using an injector device according to clause 1, the method comprising:

actuating the injector device such that a plunger rod is moved longitudinally within the hosing from a primed position to a completed position; and providing information associated with the longitudinal position of the plunger rod with an indicator.

The invention claimed is:

1. An injector device comprising:

an elongate housing having a proximal end, a proximal region, and a distal end, the housing configured to receive a container of medicament;

a plunger rod moveable longitudinally within the housing between a primed position and a completed position, the plunger rod being configured to engage with a container of medicament that is received in the housing;

wherein the housing comprises an indicator located in the proximal region of the housing; the indicator comprising:

a display window located in a side wall of the proximal region of the housing, a projection proximally extending from the plunger rod, wherein the projection is coupled to the plunger rod, the projection being visible through the display window in the primed position, and an indication element, the projection being located between the display window and the indication element to block a visibility of the indication element through the display window in the primed position, the projection being configured to move between a first indicating position and a second indicating position to provide a user with information associated with a progress of an injection process dependent upon a longitudinal position of the plunger rod, wherein the distal end of the housing is relatively closer to an injection site and the proximal end of the housing is relatively further away from the injection site.

2. The injector device of claim 1, wherein the projection is coupled to the plunger rod and configured to move between the first indicating position and the second indicating position when the plunger rod is moved from the primed position to the completed position, and wherein movement of the projection towards the second indicating position uncovers a portion of the indication element that is visible through the display window.

3. The injector device of claim 2, wherein when the projection is in the first indication position, a proximal end of the projection is located at a proximal end of the display window.

4. The injector device of claim 3, wherein when the projection is in the first indicating position, only the projection is visible through the display window.

5. The injector device of claim 2, wherein when the projection is in the second indicating position, a proximal end of the projection is located at a distal end of the display window.

6. The injector device of claim 5, wherein when the projection is in the second indicating position, only the indication element is visible through the display window.

7. The injector device of claim 1, wherein the projection is rotationally decoupled from the plunger rod such that the projection remains aligned with the display window throughout the injection process.

8. The injector device of claim 7, wherein an inner surface of the housing comprises a guide mechanism configured to restrict a rotational motion of the projection about a longitudinal axis of the plunger rod.

9. The injector device of claim 1, wherein the housing comprises a second indicator comprising a second display window in a distal region of the housing, a container of medicament being visible through the second display window when the plunger rod is in the primed position and when the container of medicament is received in the housing, and wherein when the plunger rod is moved longitudinally into the completed position, the distal end of the plunger rod is located at a distal end of the second display window.

10. The injector device of claim 9, wherein the plunger rod and the indication element comprise an indicia and the projection comprises a different indicia to the plunger rod and the indication element.

11. The injector device of claim 1, comprising an external sleeve configured to extend around the housing, the external sleeve being moveable longitudinally from a first position at the proximal end of the housing, in which the external sleeve covers the indicator, to a second position at the distal end of the housing, in which the external sleeve exposes the indicator.

12. The injector device of claim 1, comprising a container of medicament received within the housing between the plunger rod and the distal end of the housing.

13. A method of using an injector device, the injector device comprising an elongate housing having a proximal end and a distal end, wherein the distal end is relatively closer to an injection site and the proximal end is relatively further away from the injection site, the method comprising:

actuating the injector device such that a plunger rod moves longitudinally within the housing from a primed position to a completed position; and moving a proximally extending projection with the plunger rod between a first indicating position and a second indicating position revealing a greater portion of an indication element of an indicator visible through a display window to provide information associated with a longitudinal position of the plunger rod with the indicator.

* * * * *